United States Patent
Thakur et al.

(10) Patent No.: US 8,566,114 B2
(45) Date of Patent: Oct. 22, 2013

(54) COMPUTER PROGRAM PRODUCT, SYSTEM AND METHOD FOR PROVIDING SOCIAL SERVICES TO INDIVIDUALS BY EMPLOYING BI-OBJECTIVE OPTIMIZATION

(75) Inventors: Tarun Thakur, San Jose, CA (US); Kun Liu, San Jose, CA (US); Evimaria Terzi, Palo Alto, CA (US); Tyrone W. A. Grandison, San Jose, CA (US); William Cody, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 730 days.

(21) Appl. No.: 12/128,495

(22) Filed: May 28, 2008

(65) Prior Publication Data
US 2009/0299761 A1 Dec. 3, 2009

(51) Int. Cl.
G06Q 10/00 (2012.01)
G06Q 50/00 (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS

| | | | | |
|---|---|---|---|---|
| 2004/0093237 | A1* | 5/2004 | Redding et al. | 705/2 |
| 2004/0199415 | A1 | 10/2004 | Ho | |
| 2006/0161464 | A1* | 7/2006 | Green | 705/7 |
| 2006/0282410 | A1* | 12/2006 | Weitzman et al. | 707/3 |
| 2007/0088597 | A1 | 4/2007 | Herr et al. | |
| 2007/0168211 | A1* | 7/2007 | Arnebeck | 705/1 |
| 2008/0027754 | A1 | 1/2008 | Auker et al. | |

FOREIGN PATENT DOCUMENTS

EP 1329831 A1 1/2002

OTHER PUBLICATIONS

Pezzin et al. (Health Service Research 37:Aug. 4, 2002).*
Hirth et al., Worker Preferences, sorting and Aggregate Patterns of Health Insurance Coverage, Feb. 9, 2006.*
Pezzin et al. (Health Service Research 37:4, Aug. 2002).*

* cited by examiner

*Primary Examiner* — Neha Patel
(74) *Attorney, Agent, or Firm* — Cantor Colburn LLP

(57) ABSTRACT

A computer program product and a system are provided. The product and system provide associations between individuals having health care needs and available social services. The providing is efficient and cost effective.

3 Claims, 3 Drawing Sheets

COMPUTER PROGRAM PRODUCT, SYSTEM AND METHOD FOR PROVIDING SOCIAL SERVICES TO INDIVIDUALS BY EMPLOYING BI-OBJECTIVE OPTIMIZATION

TRADEMARKS

IBM® is a registered trademark of International Business Machines Corporation, Armonk, N.Y., U.S.A. Other names used herein may be registered trademarks, trademarks or product names of International Business Machines Corporation or other companies.

BACKGROUND OF THE INVENTION

1. Field of the Invention

The present invention relates to healthcare-related information sharing, and particularly to associating individuals having medical conditions with needed health care resources.

2. Description of the Related Art

Health-related social service programs (SSs) are an integral part of the American healthcare system. These programs seek to assist patients in managing their medical conditions and improving their quality of life. A few examples of these social services include In-Home Support Services (IHSS), Healthcare Insurance Premium Payment Plan, Transportation Programs, and Financial Assistance Programs (e.g. Supplemental Security Income (SSI)). While social services are in principle helpful, they tend not to be leveraged optimally because of a number of challenges associated with their design, implementation, promotion and delivery. One of the leading reasons for the under-utilization of social services is the fact that patients have limited knowledge of these programs, their associated time constraints, eligibility requirements, etc. Reference may be had to FIG. 1. This problem of not enabling patients to leverage such social service programs results in great discomfort during the recovery process.

In FIG. 1, a person is shown pondering over diagnosis of a chronic health condition, in this example, leukemia. Questions such as what social services are available for the condition, how to afford health care, how to obtain supplemental income and others are clearly relevant to persons who are diagnosed with any chronic medical conditions such as cancer, etc.

Therefore, what is needed is a robust, automated system for providing health care information, social services information, and assistance with automated access to patients.

SUMMARY OF THE INVENTION

The present invention provides a computer program product stored on machine readable media and including machine readable instructions for executing a method for associating an individual, $p_i$, from a plurality of m individuals, with at least one social service program, n, from a plurality of programs, the individual having a need for at least one social service benefit, each social service program services only one type of need, and each social service program is characterized by a cost, $c_j$, and a capacity, $k_j$, wherein the cost, $c_j$, is incurred by a service provider for establishing a need of the individual and the capacity $k_j$, is an upper bound on a number of individuals, p, the program is configured to service, the method including: identifying the individual having a need for at least one social service benefit; identifying a matrix, X, for each need, wherein each entry, $X_{ij}$, in the matrix, X, has one of two values wherein a first value corresponds to association of the individual to a service, $S_j$, and a second value corresponds to a non-association of the individual to the service, $S_j$; and associating the individual to the service, $S_j$, for each need, wherein the associating is performed according to an algorithm.

The present invention also provides a service provider for associating individuals with social services, the service provider including: a processing system for executing machine readable instructions stored on machine readable media and provided to the processing system, the instructions including instructions for for executing a method for associating an individual, $p_i$, from a plurality of m individuals, with at least one social service program, n, from a plurality of programs, the individual having a need for at least one social service benefit, each social service program services only one type of need, and each social service program is characterized by a cost, $c_j$, and a capacity, $k_j$, wherein the cost, $c_j$, is incurred by a service provider for establishing a need of the individual and the capacity $k_j$, is an upper bound on a number of individuals, p, the program is configured to service, the method including: identifying the individual having a need for at least one social service benefit; identifying a matrix, X, for each need, wherein each entry, $X_{ij}$, in the matrix, X, has one of two values wherein a first value corresponds to association of the individual to a service, $S_j$, and a second value corresponds to a non-association of the individual to the service, $S_j$; and associating the individual to the service, $S_j$, for each need, wherein the associating is performed according to an algorithm.

In a further embodiment, a service provider for associating individuals with social services is disclosed and includes: a processing system for executing machine readable instructions stored on machine readable media and provided to the processing system, the instructions including instructions for for executing a method for associating an individual, $p_i$, from a plurality of m individuals, with at least one social service program, n, from a plurality of programs, the individual having a need for at least one social service benefit, each social service program services only one type of need, and each social service program is characterized by a cost, $c_j$, and a capacity, $k_j$, wherein the cost, $c_j$, is incurred by a service provider for establishing a need of the individual and the capacity $k_j$, is an upper bound on a number of individuals, p, the program is configured to service, the method including: sorting into a first list individuals in decreasing order of priority; sorting into a second list services in increasing order of cost incurred by a service provider to establish a need of the individual; traversing the first and second lists from top to bottom, and associating every individual with a lowest possible cost service whose capacity has not been exhausted.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description below explains the preferred embodiments of the invention, together with advantages and features, by way of example with reference to the drawings.

DETAILED DESCRIPTION OF THE INVENTION

The present invention provides a computer program product and system for providing health care, social service and other related types of information. The information is generally obtained from the system and provided to a user in the context of a specific health care matter.

Accordingly, disclosed herein are embodiments that include a centralized service provider (SP), which takes as input the benefits offered by providers of social services (SSs) in the context of needs of a patient. The service provider then uses a novel method to optimally assign (e.g., associates) patients to social services that may help provide comprehensive patient care. The service provider may be very beneficial to patients with chronic diseases (such as heart disease, cancer, diabetes, etc.) who want to lead their lives as normally as possible. The service provider may be a single, real authoritative and separate entity, a virtual consolidation of disparate entities, and other embodiments as might be devised. Regardless, the service provider generally provides for satisfying needs of patients while minimizing cost of operation.

As discussed herein, minimizing cost corresponds to cost of associating patients with social services and implementing these services on the patients' behalf Formally, it may be stated that the service provider has a bi-objective goal, or a dual performance goal—minimize the cost of providing social service to a patient, and maximize the satisfaction of the patient. Accordingly, the service provider is generally designed and constructed with informatics and computer science theory in mind, such that it enables the service provider to solve problems and provide optimal solutions.

Figure 1:
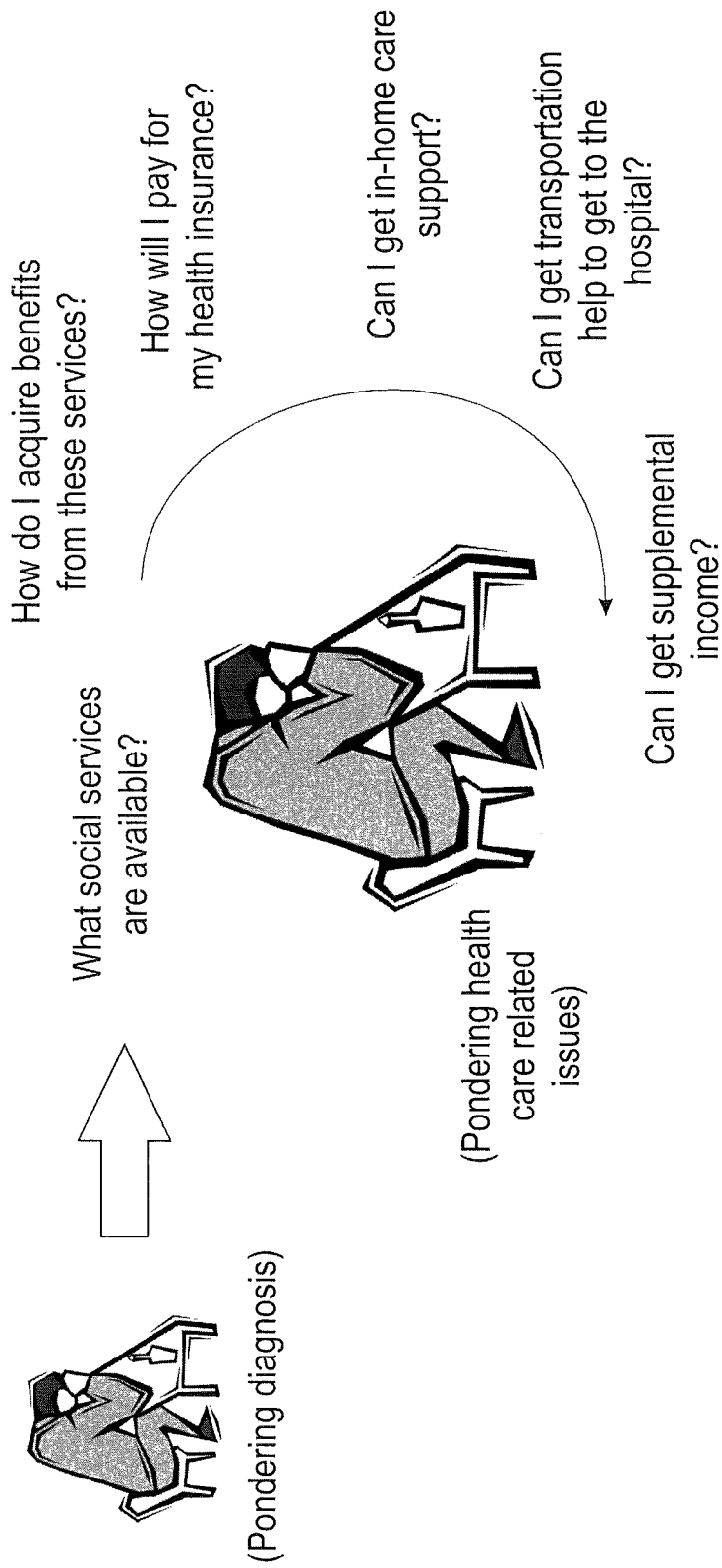
FIG. 1 illustrates one example of a patient pondering health care related issues for a medical condition.
Figure 2:
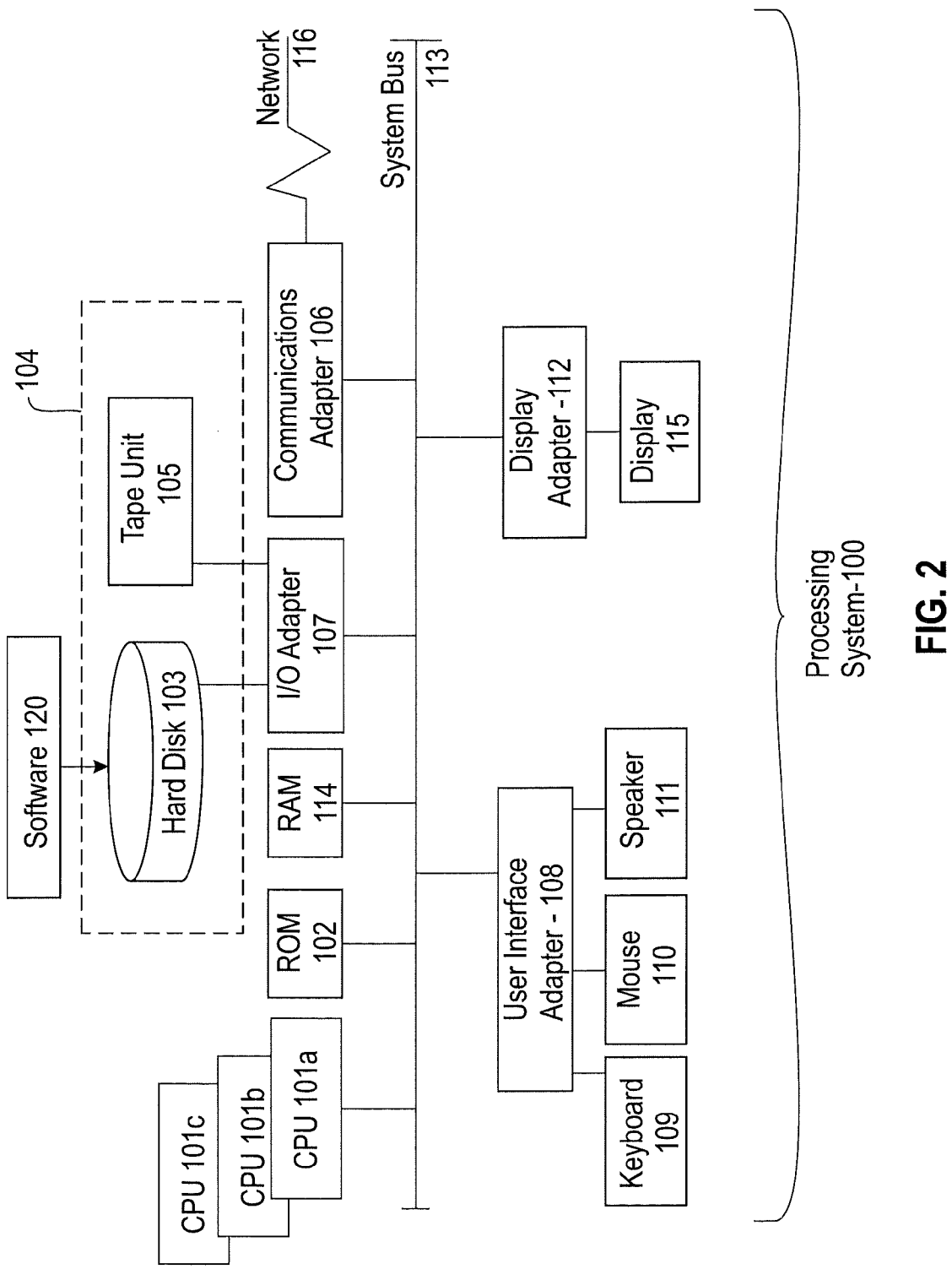
FIG. 2 illustrates one example of a computing environment for implementing the teachings herein.

Referring to FIG. 2, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 2 further depicts an input/output (I/O) adapter 107 and a network or communications adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Components Interface (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

Thus, as configured in FIG. 2, the system 100 includes processing means in the form of processors 101, storage means including system memory 114 and mass storage 104, input means such as keyboard 109 and mouse 110, and output means including speaker 111 and display 115. In one embodiment, a portion of system memory 114 and mass storage 104 collectively store an operating system such as the AIX® operating system from IBM Corporation to coordinate the functions of the various components shown in FIG. 2.

It will be appreciated that the system 100 can be any suitable computer or computing platform, and may include a terminal, wireless device, information appliance, device, workstation, mini-computer, mainframe computer, personal digital assistant (PDA) or other computing device.

Examples of operating systems that may be supported by the system 100 include Windows 95, Windows 98, Windows NT 4.0, Windows XP, Windows 2000, Windows CE, Windows Vista, Macintosh, Java, LINUX, and UNIX, or any other suitable operating system. The system 100 also includes a network interface 116 for communicating over a network. The network can be a local-area network (LAN), a metro-area network (MAN), or wide-area network (WAN), such as the Internet or World Wide Web.

Users of the system 100 can connect to the network through any suitable network interface 116 connection, such as standard telephone lines, digital subscriber line, LAN or WAN links (e.g., T1, T3), broadband connections (Frame Relay, ATM), and wireless connections (e.g., 802.11(a), 802.11(b), 802.11(g)).

As disclosed herein, the system 100 includes machine readable instructions stored on machine readable media (for example, the hard disk 104) for capture and interactive display of information shown on the screen 115 of a user. As discussed herein, the instructions are referred to as "software" 120. The software 120 may be produced using software development tools as are known in the art. The software 120 may include various tools and features for providing user interaction capabilities as are known in the art.

In some embodiments, the software 120 is provided as an overlay to another program. For example, the software 120 may be provided as an "add-in" to an application (or operating system). Note that the term "add-in" generally refers to supplemental program code as is known in the art. In such embodiments, the software 120 may replace structures or objects of the application or operating system with which it cooperates.

The software 120 may be native to (written to function within) computer application code programs (for example, C, C++, Perl, XML, HTML and others), other programs typically regarded as computing environments (UNIX, LINUX, DOS, and others) as well as other types of programs.

As a matter of convention herein, it is considered that the "software" 120 provides for dissemination of "social service information." Accordingly, it is considered that "social service information" as discussed herein may include the various forms of information and communications available from social service agencies, health care providers, insurers, governmental agencies, emergency service providers, hospitals, clinics, universities, foundations, collaborations, partnerships, third party providers, advertisers, manufacturers, retailers and other such parties that produce useful information for a user.

As may be used herein, the term "automated" generally refers to a capability of the software 120 to perform intended functions with minimal, limited or no intervention or supervision by a user.

Accordingly, in one embodiment, the software 120 is provided as a centralized service provider, (SP). The service provider (SP) takes as input the benefits offered by social services and the needs of patients and then optimally assigns patients to social services that will help provide comprehensive patient care. The software 120 is equipped to provide a variety of benefits to patients with chronic diseases such as, heart disease, cancer, diabetes, who want to lead their lives as normally as possible. In various embodiments, the software 120 is a single, real authoritative and separate entity. Alternatively, the software 120 may be a virtual consolidation of disparate entities. Any combination may be had as well. Regardless, the software 120 generally provides for, simultaneously and maximally addressing needs of a patient as well as minimizing system cost (i.e., a cost corresponding to associating patients with social services). Accordingly, it may be considered that the software 120 (i.e., service provider) has a bi-objective (or a dual objective) to satisfy.

There are assets and liabilities in the present day American social service system. On a positive side, there are a number of social services programs that offer benefits well-suited to the needs of a majority of people diagnosed with chronic medical conditions. On the negative side, there are a number of challenges associated with these social services, which effectively render them useless. Accordingly, presented below is a consideration of a number of research challenges. A simple example would be the transformation of paper-based processes adopted by the high demand health-related social services. Generally, such services are rudimentary in nature and strictly adhered to by the administrative staff who manually performs the eligibility evaluations. As an example, consider the following problems encountered in attempting to help patients acquire the social service benefits:

1. Discovery of Social Services: Currently, the information on social services is often not available in intuitive or convenient locations. This is an important concern for someone with more troubling concerns on their mind. Thus, a key concern is being able to automatically discover and identify different social services that might be available.

2. Personalization of Results: For discovered social services, it should be possible to determine the most appropriate program for a particular patient. Generally, it takes considerable time and energy to wade through information provided by social services to ascertain applicability to a user. Accordingly, the software 120 provided herein includes an intelligent engine that, given diagnosis, medical records, personal information, etc., can determine the applicable social services based on the patient's condition. This is simply referred to as the "personalization" of social services.

3. Optimal Assignment of Social Services to Patients: Given that there are social services that offer specific benefits (and have capacity constraints) and that there are patients who have specific needs (and priorities for these needs), the optimal assignment problem is how to satisfy all these requirements.

4. Automated Acquisition of Benefits from Social Service Programs: Given the current manner in which social services are structured, patients generally have to rely on labor intensive, manual, paper-based processes to work with the administrators of these social service benefits. This is a significant inhibitor to patients successfully acquiring benefits. Enabling automatic form-filling and workflow process management are important aspects of benefit acquisition.

In particular, the software 120 provides for optimally assigning social services to patients. Note that given some arbitrary criteria, alignment of social services with needs of patients is not a naive matching problem (where the system finds a match between both sides). Rather, matching is a first step (or a pre-processing step) in alignment of benefits. In particular, the software 120 is proficient in a step after matching—how to optimally assign social services to patients. The rationale behind why this problem cannot be solved by matching is that assignment of arbitrary services to arbitrary patients may not be completed even though they can be matched. We need to consider the priority of a patient's need (as a patient can have many different needs) and the capacity of the social services. Additionally, collections of patients (instead of one after another) must be considered in order to make an optimal decision.

In some embodiments, the software 120 provides a solution that is predicated on the existence of an engine that either sits at a trusted location between the patient and the service provider or sits at the patient's site, which is inherently trusted by the patient. For purposes of the example discussed herein, it is assumed that a trusted location is in the center. The engine receives input from the patients and, based on prior knowledge provided by each of the social services, executes the algorithm for optimal allocation. Consider the following example wherein a formal problem definition used by the system, an algorithm the engine implements and the experimentation performed are all presented.

Problem Formulation

When considering allocation, assume there are m patients ($p_1, \ldots, p_m$), each of whom have specific needs (e.g., a need for transportation assistance). Also, assume there are n social service programs ($S_1, \ldots, S_n$) available to satisfy needs. Every patient, $p_i$, corresponds to a real value in the interval [0, 1] that indicates the priority that the patient has for the respective need, irrespective of which social service is assigned to that patient to satisfy the need. Every $S_j$ is characterized by two values $c_j$, $k_j$ where $c_j$ corresponds to the cost incurred by the service provider (i.e., the software 120) to establish the need of a patient with $S_j$ and $k_j$ is an integer value that denotes the upper bound on the number of patients $S_j$ can serve, (i.e., capacity of $S_j$). The goal of the service provide is to maximize the overall satisfaction of the patients, minimize the total establishment cost and of course respect the hard capacity constraints of social services imposed by the bound $k_j$. Thus, the problem is to find a 0-1 assignment matrix X for every patient, (i.e. assign services to patients for that specific need). Each entry $X_{ij}$ takes values either 1 or 0 corresponding to the assignment of social service $S_j$ to patient $p_i$ or not respectively. In this example, the assignment is such that:

$$\min\left\{\sum_j k_j, m\right\} \leq \sum_{i,j} x_{ij} \leq \sum_j k_j; \text{ for every } i: \sum_j x_{ij} \leq 1. \quad (1)$$

That is, every social service can serve at most $k_j$ patients and every patient can only satisfy his needs by at most one social service. At the same time the assignment should minimize the total costs and maximize patient satisfaction (weighted by the priority). Thus, for every need k:

$$\min \Sigma_{i,j} c_j x_{ij}, \text{ and} \quad (2);$$

$$\max \Sigma_{i,j} p_i x_{ij}. \quad (3)$$

Next, the above problem is shown with two objectives that can be solved optimally by an algorithm. An example of the algorithm is provided below and referred to as "DOUBLE-SORT."

For the specific optimization problem presented, an efficient polynomial-time algorithm is presented that gives an optimal solution. First, the algorithm is described. Following the description is a proof.

The exemplary algorithm proceeds as follows:
1. Sort patients in decreasing order of $p_i$;
2. Sort social services in increasing order of $c_j$;
3. Traverse the sorted lists from top to bottom and satisfy the need of every patient with the service with the lowest possible cost whose capacity has not been yet exhausted.

As an evaluation of performance of the DOUBLESORT algorithm, consider the following proof First, it should be recognized that if there are enough social services, then all the patients can be satisfied, the overall satisfaction level is by default maximized. Since social services are chosen in increasing order of cost, the total cost is therefore minimized. Similarly, if there are not enough social services available to satisfy need, then by definition all of them will be consumed by the patients, the total cost can not be further reduced. Since the software 120 tries to satisfy patients in increasing order of their needs, the overall satisfaction level is maximized in that situation.

The run time, O, of the DOUBLESORT algorithm is dominated by the sorting of the patients and the social services and therefore may be determined as: O n log(n)+m log(m)).

It is natural that each patient could have multiple different needs. In that case, the algorithm may run independently for every need. However, it should be noted that a single social service can help each patient with respect to only one of his/her needs.

As an evaluation of the algorithm, experiments were performed on 10,000 patients to evaluate the solution provided by the software 120 against a baseline approach that randomly assigns social services to patients without considering any constraints or objectives. A simulated environment in this instance of the project was used.

In the experiments, priority values $p_i$ were chosen uniformly at random from interval [0; 1]. The costs, $c_i$, were generated from a chi-square distribution with two degrees of freedom. That is, if $\chi_i$, i=1, . . . , k, are k independent, normally distributed random variables with mean 0 and variance 1, then a random variable $\Sigma_{i-1}^{k} \chi_i$ is distributed according to the chi-square distribution, and k specifies the number of degrees of freedom.

Using this distribution, selection of social services was performed such that most of had low costs while only a few had high costs. To simulate more realistic capacity constraints, a total number of available social services was changed to make sure that only a fraction of patients could be served.

Figure 3:
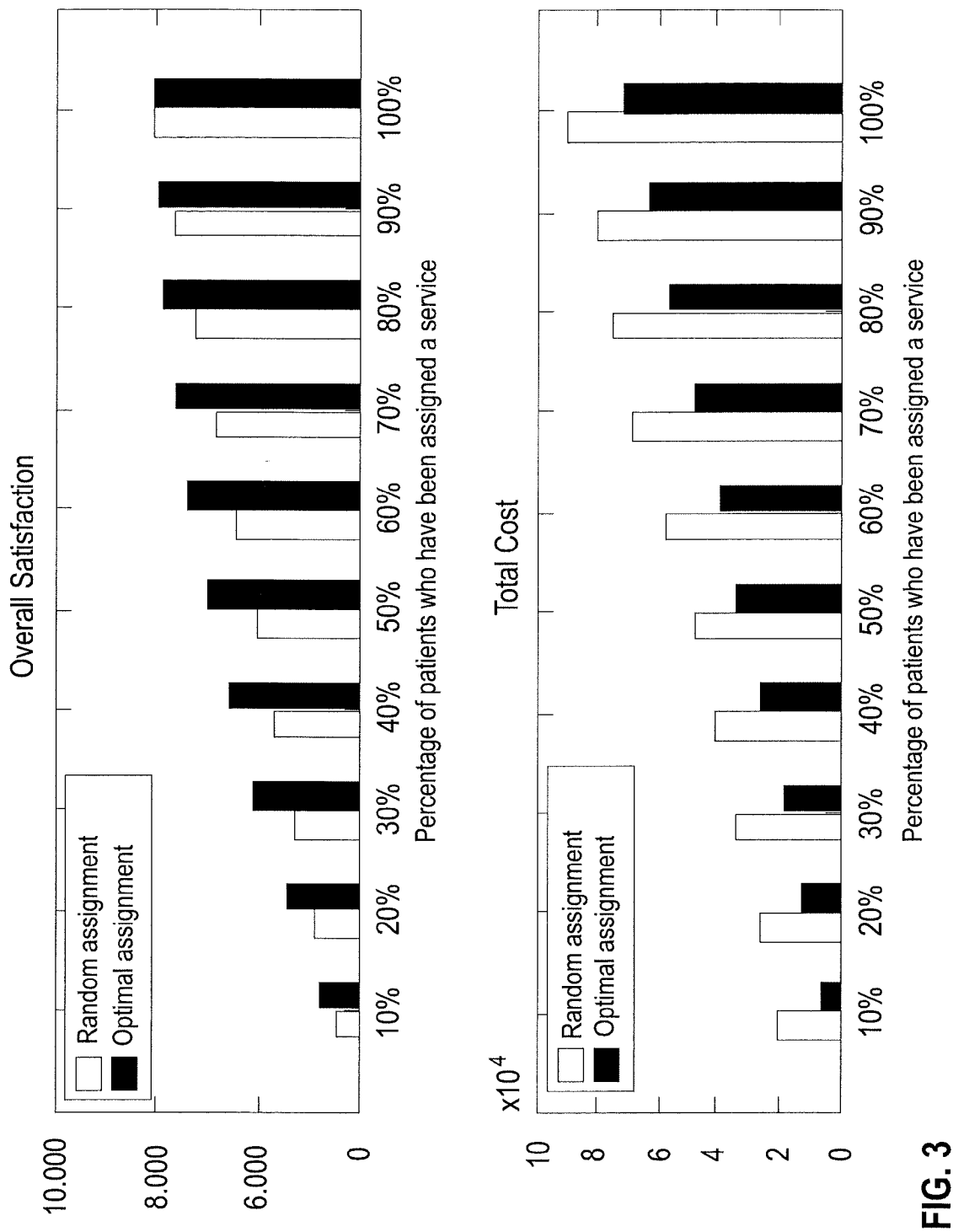
FIG. 3 depicts test result data.

Experimental results are depicted in FIG. 3. In FIG. 3, the y-axis of the top figure represents the overall satisfaction (see Equation 3), the y-axis of the bottom figure represents the total cost (see Equation 2). The x-axes of both figures implicitly represent the capacities of the available social services. It can be observed that the algorithm as described above achieves much lower cost while much higher overall satisfaction for different percentage of the patients who can be satisfied.

In a world of scarce resources and with an increased push towards the web enablement of healthcare services, it becomes very important to ensure that patients are efficiently able to leverage the social services available to them and thus get the best care possible without exerting significant cost on providers of public health services. Currently, there is a lot of attention on the computerization of operational, patient-focused activity, at the point of care. Scant effort has been placed on bridging the divide between point-in-time healthcare and the associated supporting public health resource allocations, which are needed to enable complete care management (i.e. from diagnosis to treatment to long-term service acquisition that bolsters recovery). Accordingly, presented herein are foundations for optimally associating social service programs (SSs) with patients or individuals, given their specific set of needs. Presented is a method for providing social services to patients by employing bi-objective optimization—minimize the cost to assign a social service program to a patient and maximize the satisfaction of the patient.

Although the teachings herein are geared to the American healthcare market, the observations and technology are generic and can be applied elsewhere easily. For example, aside from other jurisdictions, similar problems exist in other domains, such as how an auto insurance company assigns repair shops to a set of customers so that the cost is minimized and at the same time ensuring the customers are satisfied.

The capabilities of the present invention can be implemented in software, firmware, hardware or some combination thereof.

As one example, one or more aspects of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A computer program product comprising:
   a non-transitory computer readable storage medium having computer readable instructions stored thereon, the computer readable instructions executable by a processor to identify a plurality of individuals, each of the individuals having a corresponding social service need that is associated with a priority, the priority represented as a numerical value within a specified range;
   identify a plurality of programs, each of the programs providing a service to address only one type of social service need, and each of the programs associated with a cost and a maximum number of the individuals to be associated with the program;
   sort into a first list the individuals in decreasing order of the priority associated with the corresponding social service need such that a first entry of the first list is an individual with a corresponding social service need having a highest priority;
sort into a second list the programs in increasing order of the cost associated with each program; and
associate, in turn, each individual from the first list, beginning with the individual with the corresponding social service need having the highest priority, with a program from the second list with a lowest cost based on the program meeting a type of the corresponding social service need of the individual and the maximum number not being reached for the program, wherein
at least one of the individuals is a healthcare patient, and at least one of the programs is a healthcare program, and the associate, in turn, each individual from the list with a program from the second list is completed in a time period given by a runtime based on a sum of a logarithmic value of a total number of the programs and a logarithmic value of a total number of the individuals.

2. A system comprising:
a memory having computer readable instructions; and
a processor for executing the computer readable instructions, the instructions including:
identifying a plurality of individuals, each of the individuals having a corresponding social services need that is associated with a priority, the priority represented as a numerical value within a specified range;
identifying a plurality of programs, each of the programs providing a service to address only one type of social service need, and each of the programs associated with a cost and a maximum number of the individuals to be associated with the program;
sorting into a first list the individuals in decreasing order of the priority associated with the corresponding social service need such that a first entry of the first list is an individual with a corresponding social service need having a highest priority,
sorting into a second list the programs in increasing order of the cost associated with each program; and
associating, in turn, each individual from the first list, beginning with the individual with the corresponding social service need having the highest priority, with a program from the second list with a lowest cost based on the program meeting a type of the corresponding social service need of the individual and the maximum number not being reached for the program, wherein
at least one of the individuals is a healthcare patient, and at least one of the programs is a healthcare program, and the associating, in turn, each individual from the first list with a program from the second list is completed in a time period given by a runtime based on a sum of a logarithmic value of a total number of the programs and a logarithmic value of a total number of the individuals.

3. A method comprising:
identifying a plurality of individuals, each of the individuals having a corresponding social services need that is associated with a priority, the priority represented as a numerical value within a specified range;
identifying a plurality of programs, each of the programs providing a service to address only one type of social service need, and each of the programs associated with a cost and a maximum number of the individuals to be associated with the program;
sorting into a first list, by a computer processor, the individuals in decreasing order of the priority associated with the corresponding social service need such that a first entry of the first list is an individual with a corresponding social service need having a highest priority,
sorting into a second list, by the computer processor, the programs in increasing order of the cost associated with each program; and
associating, in turn, by the computer processor, each individual from the first list, beginning with the individual with the corresponding social service need having the highest priority, with a program from the second list with a lowest cost based on the program meeting a type of the corresponding social service need of the individual and the maximum number not being reached for the program, wherein
at least one of the individuals is a healthcare patient, and at least one of the programs is a healthcare program, and the associating, in turn, each individual from the first list with a program from the second list is completed in a time period given by a runtime based on a sum of a logarithmic value of a total number of the programs and a logarithmic value of a total number of the individuals.

* * * * *